United States Patent
Chawathe et al.

(10) Patent No.: US 10,711,177 B2
(45) Date of Patent: Jul. 14, 2020

(54) ENGINEERING FORMATION WETTABILITY CHARACTERISTICS

(71) Applicant: Chevron U.S.A. Inc., San Ramon, CA (US)

(72) Inventors: Adwait Chawathe, Sugar Land, TX (US); Nariman Fathi Najafabadi, Sugar Land, TX (US); Jagannathan Mahadevan, Sugar Land, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 16/380,735

(22) Filed: Apr. 10, 2019

(65) Prior Publication Data

US 2019/0233713 A1    Aug. 1, 2019

Related U.S. Application Data

(63) Continuation of application No. 15/073,302, filed on Mar. 17, 2016, now Pat. No. 10,301,532.
(Continued)

(51) Int. Cl.
*E21B 43/16* (2006.01)
*C09K 8/58* (2006.01)
(Continued)

(52) U.S. Cl.
CPC .............. *C09K 8/58* (2013.01); *C09K 8/845* (2013.01); *E21B 43/16* (2013.01); *G16C 20/30* (2019.02)

(58) Field of Classification Search
CPC . C09K 8/58; E21B 43/16; E21B 43/20; E21B 43/26; E21B 21/00
See application file for complete search history.

(56) References Cited

U.S. PATENT DOCUMENTS 172,187 A    1/1876 Sinclair
3,160,205 A    12/1964 Harvey et al.
(Continued)

FOREIGN PATENT DOCUMENTS

WO    2008070990 A1    6/2008
WO    2014025847 A1    2/2014
(Continued)

OTHER PUBLICATIONS

Alshaikh, Murtadha, et al.; "Impact of Brine Composition on Calcite Wettability: A Sensitivity Study"; 2016, SPE 172187-PA, pp. 1-13.
(Continued)

*Primary Examiner* — Silvana C Runyan

(57) ABSTRACT

Embodiments herein select a brine composition to be injected into a formation to alter wettability at a surface of the formation to enhance recovery of hydrocarbons from the formation. One embodiment comprises providing: a plurality of substrates representative of a formation, a plurality of brine compositions, and a plurality of reducing agents characterized as yielding oxyanions when added to an aqueous stream. The embodiment comprises selecting a brine composition with at least one reducing agent to be injected into the formation to alter wettability at a surface of the formation to enhance recovery of hydrocarbons from the formation and injecting the selected brine composition into the formation to alter wettability at the surface of the formation to enhance recovery of the hydrocarbons from the formation. The brine composition is selected based on interactions between the plurality of substrates, the plurality of brine compositions, and the plurality of reducing agents.

15 Claims, 12 Drawing Sheets

Related U.S. Application Data

(60) Provisional application No. 62/135,834, filed on Mar. 20, 2015.

(51) Int. Cl.
    *C09K 8/84* (2006.01)
    *G16C 20/30* (2019.01)

(56) References Cited

U.S. PATENT DOCUMENTS

| | | | |
|---|---|---|---|
| 3,252,904 | A | 5/1966 | Carpenter |
| 3,258,072 | A * | 6/1966 | Froning ............... C09K 8/845 166/252.1 |
| 3,523,582 | A | 8/1970 | Fulford |
| 3,648,772 | A | 3/1972 | Earlougher, Jr. |
| 3,800,872 | A | 4/1974 | Friedman |
| 4,746,687 | A | 5/1988 | Ryles et al. |
| 4,813,463 | A | 3/1989 | Ziegler |
| 4,852,652 | A | 8/1989 | Kuehne |
| 5,755,972 | A | 5/1998 | Hann et al. |
| 7,703,516 | B2 | 4/2010 | Hills et al. |
| 7,934,544 | B2 | 5/2011 | Hitzman et al. |
| 8,211,837 | B2 | 7/2012 | Weerasooriya et al. |
| 8,235,110 | B2 | 8/2012 | Larter et al. |
| 8,362,767 | B2 | 1/2013 | Hrlimann et al. |
| 8,372,786 | B2 | 2/2013 | Berkland et al. |
| 8,372,788 | B2 | 2/2013 | Weerasooriya et al. |
| 8,550,164 | B2 | 10/2013 | Al-Yousef et al. |
| 8,622,134 | B2 * | 1/2014 | Pauls ............... C09K 8/76 166/305.1 |
| 8,657,000 | B2 | 2/2014 | Willingham et al. |
| 8,662,171 | B2 | 3/2014 | Lumsden et al. |
| 8,679,324 | B2 | 3/2014 | Subramaniyam |
| 8,739,869 | B2 | 6/2014 | Willingham et al. |
| 8,753,865 | B2 | 6/2014 | Hendrickson et al. |
| 8,895,483 | B2 | 11/2014 | Milne et al. |
| 8,939,211 | B2 | 1/2015 | McGuire et al. |
| 10,301,532 | B2 | 5/2019 | Mahadevan et al. |
| 2005/0161219 | A1* | 7/2005 | Hossaini ........... H01L 27/14636 166/278 |
| 2010/0006283 | A1 | 1/2010 | Collins et al. |
| 2011/0035154 | A1* | 2/2011 | Kendall ............... C04B 7/364 702/14 |
| 2011/0256085 | A1 | 10/2011 | Talingting Pabalan et al. |
| 2011/0306525 | A1 | 12/2011 | Lighthelm |
| 2012/0067570 | A1 | 3/2012 | Pone |
| 2012/0125603 | A1 | 5/2012 | Wllingham et al. |
| 2012/0125604 | A1* | 5/2012 | Willingham ............... C09K 8/58 166/270.1 |
| 2012/0125605 | A1 | 5/2012 | Willingham et al. |
| 2012/0214713 | A1 | 8/2012 | Mu et al. |
| 2013/0020082 | A1 | 1/2013 | Lumsden |
| 2013/0035266 | A1 | 2/2013 | Dexter |
| 2014/0034306 | A1 | 2/2014 | Southwick et al. |
| 2014/0038858 | A1 | 2/2014 | Southwick et al. |
| 2014/0073541 | A1* | 3/2014 | Ravikiran ............... C09K 8/584 507/254 |
| 2014/0151041 | A1 | 6/2014 | Hernandez Altamirano et al. |
| 2014/0367098 | A1 | 12/2014 | Likhanova et al. |
| 2016/0272873 | A1 | 9/2016 | Mahadevan et al. |

FOREIGN PATENT DOCUMENTS

| | | |
|---|---|---|
| WO | 2014025863 A3 | 2/2014 |
| WO | 2015017190 A2 | 2/2015 |

OTHER PUBLICATIONS

Alshaikh, Murtadha, et al.; "Impact of Brine Composition on Carbonate Wettability: A Sensitivity Study"; Apr. 2014, SPE-172187-MS, pp. 1-14.

Austad, T., et al.; "Seawater as IOR Fluid in Fractured Chalk"; SPE 93000, (Feb. 2005), pp. 1-10.

Austad, T., et al.; "Seawater in Chalk: An EOR and Compaction Fluid"; SPE 118431, (Aug. 2008), pp. 648-654.

Chandrasekhar, S., et al.; "Wettability Alteration with Brine Composition in High Temperature Carbonate Reservoirs"; SPE 166280, (2013), pp. 1-17.

Dennis, D.M., et al.; "Advanced Nitrate-Based Technology for Sulfide Control and Improved Oil Recovery"; SPE 106154, (2007), pp. 1-10.

Gupta, R., et al., "Wettability Alteration of Fractured Carbonate Reservoirs"; SPE 113407, pp. 1-13.

Ma, Shouxiang, et al.; "Generalized Scaling of Spontaneous Imbibition Data for Strongly Water-Wet Systems"; 1997, Journal of Petroleum Science and Engineering, vol. 18, pp. 165-178.

Puntervold, Tina, et al.; "Injection of Seawater of Mixtures with Produced Water into North Sea Chalk Formation: Impact on Wettability, Scale Formation, and Rock Mechanics Caused by Fluid-Rock Interation"; SPE 111237, (Oct. 2007), pp. 1-12.

Strand, Skule, et al.; "Wettability Alteration of Carbonates—Effects of Potential Determining Ions (Ca2+ and SO42−) and Temperature"; (2016), Colloids and Surfaces A: Physicochem Eng. Aspects, vol. 275, pp. 1-10.

Tweheyo, M.T., et al.; "The Effects of Temperature and Potential Determining Ions Present in Seawater on Oil Recovery from Fractured Carbonates"; SPE 99438, (Apr. 2006), pp. 1-10.

Wikipedia Definition of Sodium Dithionite: http://en.wikipedia.org/wiki/Sodium-dithionite.

Zhang, Y., et al.; "Waterflood Performance by Injection on Brine with Different Salinity for Reservoir Cores"; SPE 109849, (Nov. 2007), pp. 1-12.

International Search Report, dated Jun. 15, 2016, during the prosecution of International Application No. PCT/US2016/022939.

Written Opinion of the International Searching Authority, dated Jun. 15, 2016, during the prosecution of International Application No. PCT/US2016/022939.

Eurasian Office Action, dated Oct. 29, 2019, during the prosecution of Eurasian Application No. 201792079.

* cited by examiner

ENGINEERING FORMATION WETTABILITY CHARACTERISTICS

CROSS REFERENCE TO RELATED APPLICATIONS

The present application claims priority and benefit as a continuation patent application from U.S. application Ser. No. 15/073,302 that is now U.S. Pat. No. 10,301,532, filed on Mar. 17, 2016, which is incorporated by reference in its entirety. This application claims benefit under 35 USC 119 of U.S. Provisional Patent App. No. 62/135,834 with a filing date of Mar. 20, 2015, which is incorporated herein by reference in its entirety and for all purposes. This patent application is co-pending with U.S. application Ser. No. 16/380,681 that is now U.S. Publication No. 2019/0233712, also filed on Apr. 10, 2019, which is incorporated by reference in its entirety.

TECHNICAL FIELD

The present specification relates generally to enhanced recovery of fluids from a subterranean formation, and more particularly, systems and methods for optimizing wettability of a hydrocarbon bearing formation.

BACKGROUND

The term "wettability" refers to the adhesion tension, or the tendency of a particular fluid to spread on or adhere to a solid surface in the presence of another immiscible fluid. The term "formation wettability" refers to the ability of a rock surface to preferentially contact a particular fluid. It is a function of the solid-liquid-liquid interfacial tension and determines which fluid (oil or water) will preferentially wet (adhere to) the solid surface of the rock. If the adhesion tension is large, the denser phase liquid will readily spread out and tend to coat the surface of the rock. If the adhesion tension is small, the denser fluid will only be weakly attracted to the surface. Formation wettability can affect the formation's properties such as, but not limited to, relative permeability, capillary pressure, fluid location, fluid flow, and residual oil distribution. By changing the rock character to be more water-wet, oil will flow more freely rather than being bound to the rock surface.

Formations tend to be fractured due to geologic and tectonic activity. Thus the rock matrix, within which the oil is contained, is often surrounded by fractures which are much more conductive to flow than the rock matrix itself. Under fractured rock conditions, an imbibition process, a process by which injected brine is spontaneously sucked into the rock and ejects oil simultaneously, is the main mechanism of recovery of oil. When a formation is not fractured, the main mechanism may simply be a physical displacement process also known as viscous displacement. In either case, wettability of the rock must be converted to water-wet conditions partially or fully so that the oil will flow more freely rather than being bound to the rock surface.

Under oil-wet conditions, the oil tends to be retained by the rock and hence results in low mobility of the oil. The low mobility of the oil in turn results in poor recovery of the oil from the formation. As an example, carbonate rocks tend to be more oil-wet in many cases and mixed-wet in some cases. It is desirable to engineer wettability and optimize wettability alteration in order to obtain improved recovery from rock systems.

Therefore, there exists a need to "optimize" or engineer wettability characteristics of formations to improve oil production methods and strategy.

SUMMARY OF THE INVENTION

In one aspect, provided herein are embodiments of a method to enhance recovery of hydrocarbons from a formation by altering wettability at a surface of the formation towards more water-wet. The method includes providing a formation; providing an aqueous stream for injecting into the formation; adding a reducing agent to the aqueous stream; and injecting the aqueous stream with the reducing agent into the formation to alter a surface charge of the surface of the formation to become more water-wet to enhance recovery of hydrocarbons from the formation. The reducing agent is responsive to characteristics of the formation, characteristics of brine of the formation, and characteristics of hydrocarbons of the formation.

In another aspect, provided herein are embodiments of a method to enhance recovery of hydrocarbons from a formation by altering wettability at a surface of the formation towards more water-wet. The method includes providing the formation and treating the surface of the formation by injecting an aqueous stream containing a sufficient amount of a reducing agent. The reducing agent when added to the aqueous stream yields a sufficient amount of oxyanions to change a surface charge to a more negative value to make the surface of the formation more water-wet to enhance recovery of hydrocarbons from the formation. The method further includes flooding the formation with a sufficient amount of surfactant to recover hydrocarbons from the formation. The sufficient amount of the surfactant is at least 10% less than an amount of surfactant required for equivalent recovery of hydrocarbons without the treatment of the surface of the formation with the reducing agent.

In another aspect, provided herein are embodiments of a method to select a brine composition to be injected into a formation to alter wettability at a surface of the formation towards more water-wet to enhance recovery of hydrocarbons from the formation. The method includes providing a plurality of substrates representative of the formation; providing a plurality of brine compositions; and providing a plurality of reducing agents characterized as yielding oxyanions when added to the aqueous stream. The oxyanions are selected from carbonate ($CO_3^{2-}$), nitrate ($NO_3^-$), metabisulfite ($[S_2O_5]^{2-}$), bisulfite ($HSO_3^-$), dithionite ($[S_2O_4]^{2-}$), sulfate ($SO_4^{2-}$), or any combination thereof. The method further includes conducting an uncertainty analysis using various combinations of the substrates, the brine compositions, and the reducing agents; correlating results from the uncertainty analysis to determine interactions between the reducing agents, the brine compositions, and concentration of the reducing agents with wettability altering characteristics; and using the correlated results from the uncertainty analysis to select a brine composition with at least one reducing agent to inject into the formation to enhance recovery of the hydrocarbons from the formation.

DETAILED DESCRIPTION

Figure 1A:
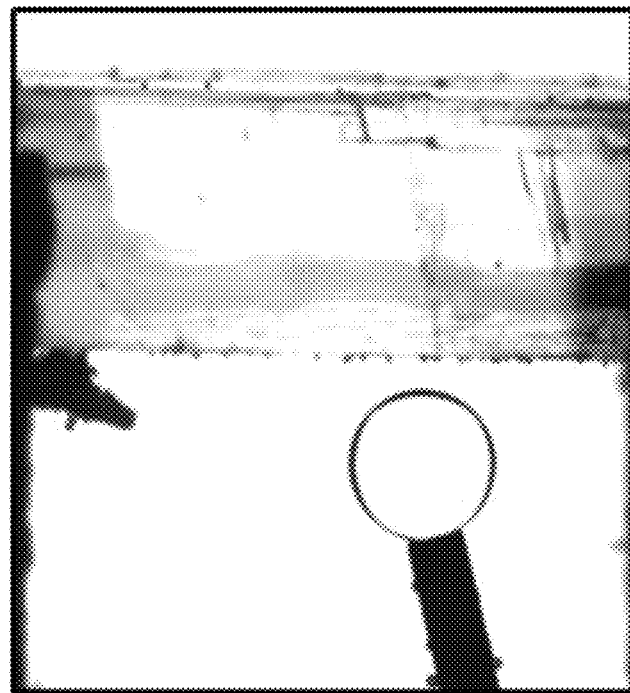
FIGS. 1A-1B are photographs featuring a droplet of an alkane on a surface of a carbonate mineral with an intervening brine layer.

"Imbibition" refers to the displacement of one fluid by another immiscible fluid. The term "water imbibition" refers to the displacement of a fluid (e.g., hydrocarbons) in a porous media (e.g., rock) by water. As used herein, the term "water" refers to water that can be pure or near-pure (e.g., greater than about 90% by weight).

"Formation" is a body of rock that is sufficiently distinctive and continuous that it can be mapped using geological methods. A formation may contain hydrocarbons, for example, oil or other hydrocarbons. A reservoir can include at least one hydrocarbon bearing formation. The term formation is not limited to the description herein. The terms formation and reservoir are sometimes used interchangeably.

"Aqueous stream", as used herein, may be practically any fluid, such as a brine, that may be injected into the formation. The aqueous stream may include various components in different concentrations. The aqueous stream may also have a particular ionic composition. The aqueous stream may be injected into the formation. One or more than one aqueous stream may be used herein. In one embodiment, an aqueous stream may be a brine (and the brine itself may or may not have other components). The term aqueous stream may be used interchangeably with the term injectant, displacing fluid, injection stream, or injection fluid.

"Optimized aqueous stream" is an aqueous stream that is likely to increase the oil recovery from the formation. An aqueous stream may be an "optimized aqueous stream" when it includes one or more reducing agents. Examples of the reducing agents include, but are not limited to, sodium carbonate, sodium nitrate, sodium bisulfite, sodium meta bisulfite, sodium dithionite, sodium sulfate, or any combinations thereof. In one embodiment, an optimized aqueous stream may be a brine with at least one reducing agent (and the brine itself may or may not have other components). In one embodiment, an optimized aqueous stream may be a brine with at least one reducing agent and at least one surfactant (and the brine itself may or may not have other components). In one embodiment, an optimized aqueous stream may be a brine with at least one reducing agent and at least one mobility control agent (and the brine itself may or may not have other components). In one embodiment, an optimized aqueous stream may be a brine with at least one reducing agent, at least one surfactant, and at least one mobility control agent (and the brine itself may or may not have other components). In one embodiment, an optimized aqueous stream may be a brine with an additive, and the additive includes at least one reducing agent (and the brine itself may or may not have other components), and so on.

"Additive" is any chemical compound that can be added to an aqueous stream. In one embodiment, the additive may include the reducing agent and at least one other component, and this additive can be added to the aqueous stream. However, in one embodiment, an additive could simply be the reducing agent. In one embodiment, the additive could be a salt. In one embodiment, the additive could be a surfactant. In one embodiment, the additive could be a polymer.

"Reducing agent" is an additive, that when hydrolyzed, can generate an oxyanion and/or change wettability of the formation towards more water wet. Examples of the reducing agents include, but are not limited to, sodium carbonate, sodium nitrate, sodium bisulfite, sodium meta bisulfite, sodium dithionite, sodium sulfate, or any combinations thereof. Of note, sometimes bisulfite is spelled as bisulphite. At least one reducing agent may be used to make the formation more water-wet.

"Oxyanion" (or oxoanion) refers to chemicals having the formula $A_xO_y^{z-}$, where A represents a chemical element and O represents an oxygen atom. Examples include, but are not limited to, carbonate ($CO_3^{2-}$), nitrate ($NO_3^-$), metabisulfite ($[S_2O_5]^{2-}$), bisulfite ($HSO_3^-$), dithionite ($[S_2O_4]^{2-}$), sulfate ($SO_4^{2-}$), or any combination thereof.

"Mobility control agent" is an additive that increases viscosity of the aqueous stream to reduce its mobility and improve the hydrocarbon recovery. In one embodiment, the mobility control agent is a polymer dissolved in or co-injected with the aqueous stream (e.g., brine). In another embodiment, the mobility control agent is a foam. For example, the mobility control agent may be formed by co-injection of a gas phase with the aqueous stream containing a surfactant (or plurality of surfactants and other chemicals), or alternate injection of aqueous stream containing a surfactant (or plurality of surfactants and other chemicals) and a gas (e.g., nitrogen), each of which may lead to generation of the foam in the formation that may increase the viscosity of the aqueous stream. In another embodiment, the mobility control agent may be formed by co-injection of the aqueous stream with liquid $CO_2$ containing a surfactant (or plurality of surfactants and other chemicals), or alternate injection of the aqueous stream and liquid $CO_2$ containing a surfactant (or plurality of surfactants and other chemicals), all of which may lead to generation of foam in the formation that increases viscosity of the aqueous stream.

"Brine" may be a sample of the brine in the formation. In some instances, brine may be a synthetic brine that is created to represent the brine in the formation. In some instances, brine may be synthetic brine that is created to constitute the aqueous stream (but the brine may or may not represent the brine in the formation).

"Substrate" is a piece of rock. The substrate may be obtained from the formation or it may be chosen to represent the formation (e.g., from an outcrop rock or even a pure mineral crystal such as calcite, mica, quartz, etc.).

"Predetermined" refers to a known quantity and it can be variable.

"Displacing phase" is a phase used to drive the hydrocarbons out of a hydrocarbon bearing formation.

"Produced brine" is the aqueous phase that is produced from the formation. This aqueous phase can have many dissolved solids including anions (e.g., chloride or sulfite) and cations (e.g., sodium, potassium, magnesium, etc.).

"Siliceous formation" is a formation that is mainly comprised of silicate materials (e.g., containing anionic silicon with the formula $(SiO_{2+n})^{2n-}$ and may contain significant amounts of clays and other minerals (e.g., gypsum, feldspar, etc.). Most siliceous formations develop by deposition into oceans and/or water streams of eroded rock materials from the Earth's surface. A siliceous formation may be referred to as a clastic formation.

"Carbonate formation" is a formation that is mainly comprised of calcium carbonate ($CaCO_3$), calcium magnesium carbonate ($CaMg(CO_3)_2$), or any combination thereof.

"Produced fluid" includes produced brine and produced hydrocarbons (liquid or gas) that are produced from the formation.

"Reservoir condition" is a commonly used term by those of ordinary skill in the art that refers to the in-situ temperature, pressure, pH, wettability, and other characteristics of the formation.

"Secondary oil recovery" refers to injection of the optimized aqueous stream before any other aqueous stream is injected into the formation or before other enhanced oil recovery methods are used to increase oil recovery from the formation.

"Tertiary oil recovery" refers to injection of the optimized aqueous stream after other aqueous streams are injected into the formation or after other enhanced oil recovery methods are used to increase oil recovery from the formation.

"Zeta potential" is a parameter characterizing electrochemical equilibrium on interfaces, where the zeta potential depends on the properties of liquid as well as on properties of the surface. Zeta potential may be calculated from electrophoretic mobility measurements in which an electrical current is passed via electrodes through an aqueous suspension consisting essentially of formation mineral colloidal particles, and determining the direction and speed of the colloidal movement. Zeta potential can be measured using electrochemical sensing technology using commercially available instruments.

"Formation wettability" may be used interchangeably with "reservoir wettability".

"Uncertainty analysis" is practically any methodology that identifies the interactions of uncertain parameters and helps in arriving at a more optimized (or optimal) solution. Examples of uncertainty analysis may include Design of Experiments, Karhunen-Loeve transform, Principal Component Analysis (PCA), sensitivity analysis, or any combination thereof. Other types of uncertainty analysis may be utilized in addition to and/or as an alternative to the examples provided herein.

For the purposes of this specification and appended claims, unless otherwise indicated, all numbers expressing quantities, percentages or proportions, and other numerical values used in the specification and claims, are to be understood as being modified in all instances by the term "about." The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%. Accordingly, unless indicated to the contrary, the numerical parameters set forth in this specification and attached claims are approximations that can vary depending upon the desired properties sought to be obtained by the present invention.

It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. For example, as used in this specification and the following claims, the terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein. By way of example, if a composition is described herein as including a component of type A, a component of type B, a component of type C, or any combination thereof, it is understood that this phrase describes all of the various individual and collective combinations and permutations of these components. For example, in some embodiments, the composition described by this phrase could include only a component of type A. In some embodiments, the composition described by this phrase could include only a component of type B. In some embodiments, the composition described by this phrase could include only a component of type C. In some embodiments, the composition described by this phrase could include a component of type A and a component of type B. In some embodiments, the composition described by this phrase could include a component of type A and a component of type C. In some embodiments, the composition described by this phrase could include a component of type B and a component of type C. In some embodiments, the composition described by this phrase could include a component of type A, a component of type B, and a component of type C. In some embodiments, the composition described by this phrase could include two or more components of type A (e.g., A1 and A2). In some embodiments, the composition described by this phrase could include two or more components of type B (e.g., B1 and B2). In some embodiments, the composition described by this phrase could include two or more components of type C (e.g., C1 and C2). In some embodiments, the composition described by this phrase could include two or more of a first component (e.g., two or more components of type A (A1 and A2)), optionally one or more of a second component (e.g., optionally one or more components of type B), and optionally one or more of a second component (e.g., optionally one or more components of type C). In some embodiments, the composition described by this phrase could include two or more of a first component (e.g., two or more components of type B (B1 and B2)), optionally one or more of a second component (e.g., optionally one or more components of type A), and optionally one or more of a second component (e.g., optionally one or more components of type C). In some embodiments, the composition described by this phrase could include two or more of a first component (e.g., two or more components of type C (C1 and C2)), optionally one or more of a second component (e.g., optionally one or more components of type A), and optionally one or more of a second component (e.g., optionally one or more components of type B).

Unless defined otherwise, all technical and scientific terms used herein have the same meanings as commonly understood by one of skill in the art to which the disclosed invention belongs.

This written description uses examples to disclose the invention, including the best mode, and also to enable any person skilled in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated herein by reference.

The specification relates to methods to enhance oil recovery from formations. More specifically, provided herein are embodiments of a method to select a brine composition to be injected into a formation to alter wettability at a surface of the formation towards more water-wet. Provided herein are also embodiments of a method to enhance recovery of hydrocarbons from a formation by altering wettability at a surface of the formation towards more water-wet. By doing so, an optimized aqueous stream (or more optimized aqueous stream) may be created and injected into the formation to alter the wettability of the formation towards more water-wet, which may in turn lead to higher oil recovery from the more water-wet formation.

Those of ordinary skill in the art may appreciate that the embodiments provided herein may facilitate identification and/or selection of reducing agents for use in the composition of brine ("brine composition") to alter wettability towards more water-wet, and hence higher oil recovery from the formation. The brine composition is tailored for the specific formation and changing the wettability characteristics of the specific formation towards water-wet (or to a state that is not oil wet) increases oil recovery. The brine chemistry optimization results in either imbibition of water or brine, or a redistribution of the wetting phase, when wettability is altered in the formation.

Those of ordinary skill in the art may appreciate that the embodiments provided herein may also be used to reduce retention of surfactants in rock systems in applications of enhanced oil recovery. For example, the surfactants may be recovered from produced brine after the oil is separated from the produced brine, and the surfactants may be recycled. In recycling the recovered surfactant, the recovered surfactant may be used as is or additional surfactant may be combined with the recovered surfactant to achieve a desired surfactant concentration.

Those of ordinary skill in the art may appreciate that the embodiments provided herein may be applicable to different types of formations, including fractured formations and formations that are not fractured. For example, the embodiments provided herein may be applicable to carbonate formations. Carbonate formations (fractured and unfractured) typically display an oil-wet tendency (lower mobility of oil compared to that of water) due to the positive surface electrical charge on the carbonate mineral at reservoir conditions when pH, an indicator for acidity or alkalinity of a solution, is near neutral. Because of the oil-wet tendency, carbonate formations tend to have poor oil recovery due to the low mobility of the wetting phase. The embodiments provided herein may also apply to siliceous formations, for example, sandstone formations (e.g., sandstone formations including quartz minerals), or other formations. For simplicity, the disclosure will focus on carbonate formations, but this specification is not limited to carbonate formations.

Wettability Engineering & Alteration:

Wettability, or the ability of the oil to coat the rock mineral surface, controls the flow process in a carbonate rock medium having small connected pore spaces. Under reservoir conditions, the oil-brine interface may be negatively charged due to the de-protonation of the organic acids (e.g., carboxylic acids). However, due to the electrostatic interaction between the oppositely charged interfaces, the oil prefers to coat the carbonate surface (i.e., oil-wet conditions) and therefore the oil tends to be retained by the carbonate rock, resulting in low mobility of the oil. Other mechanisms for the development of oil-wet conditions are known in the art that may apply to siliceous and/or carbonate formations, including adsorption of naturally occurring hydrocarbon surfactants on to the surface of the formation.

In one embodiment, the invention relates to a method to engineer wettability and engineer wettability alteration in order to obtain improved recovery from formations, by changing the wettability of the formation to partial or fully water-wet condition. The alteration is for either fractured or non-fractured formations. Formations tend to be fractured due to geologic and tectonic activity. The rock matrix, within which the oil is contained, is often surrounded by fractures which are much more conductive to flow than the rock matrix itself. Under fractured rock conditions, an imbibition process in which injected brine is spontaneously sucked into the formation and ejects oil simultaneously is the main mechanism of recovery of oil. If the rock is oil-wet, the oil prefers to stay in the matrix and does not migrate into the fractures.

When the formation is not fractured, the main mechanism is a physical displacement process (viscous displacement), and the recovery of oil is much easier than when the rock is fractured. The aqueous stream traverses through the porous rock matrix thereby displacing the oil from the rock physically. The forces that govern this process are typically associated with the capillary nature of the formation and the extent of pressure applied to the aqueous stream. An oil-wet carbonate rock tends to hold onto the oil phase preferentially, causing a poor movement of oil and channeling of the injected secondary fluid. When the rock is made water-wet from an oil-wet condition, the process of displacement is more efficient as the oil is free to move towards the production well.

Methods to Select Additives to Alter Wettability:

In one embodiment, the invention relates to a method for the selection of additives (e.g. reducing agent) to alter wettability in carbonate formations, e.g., calcium rich formations ("calcite mineral system"), with retrograde solubility in which it becomes less soluble in water as the temperature increases. In a calcite mineral system, because the surface is positively charged under neutral pH conditions, the surface potential would need to be turned to negative potential. In one embodiment to produce a negatively charged surface, electron donors or ionic components that can lead to a charge transfer to the calcite mineral surface are employed. Once the charge transfer is accomplished, the interface of calcite and brine is negatively charged and when the oil-brine interface is negatively charge, a water-wet condition results. The method can also be used for most siliceous system (e.g., sandstone formations including quartz minerals).

Divalent cations and anions (which act as conjugate acids and bases respectively) such as magnesium, barium, etc., and sulfate, carbonate, etc., lead to changes in the surface charge without necessarily leading to surface hydrocarbon coverage change. The electrochemical potential difference of the additive (e.g. reducing agent) when the electrolyte contains simple and isolated conjugate acid and/or conjugate base, is described by the Nernst equation.

The Nernst equation is:

$$E_{cell} = E^o_{cell} - \frac{RT}{zF} \ln Q_r,$$

where T is temperature, R is universal gas constant (R=8.314472 J/(K mole), F is Faraday's constant (number of coulombs per mole of electrons; F=9.648534e4 C/mole), z is the number of moles of electrons transferred in the cell reaction, $Q_r$ is the reaction quotient, $E_{cell}$ is cell electromotive force at temperature T, and $E_{cell}^o$ is the standard cell electromotive force.

Salts of weak acids (which result in a strong conjugate base) and salts of strong acids (which result in strong bases) both ionize in aqueous solutions to produce anions with reducing properties or ability to offer electrons to the calcite mineral surface. Adsorption of these anions also cause charge transfer and hence surface potential change to the carbonate formation. The surface potential change, due to changes in surface charge, leads to changes in streaming potential during flow conditions. The surface potential change can be measured to obtain zeta potential to identify reducing agents.

The wettability of the formation can be altered with the addition of at least one reducing agent that when added to an aqueous stream (e.g., brine) yields a sufficient amount of oxyanions to change the surface charge to a more negative values (e.g., a reduction in surface charge value of coulomb per meter or $C/m^2$). Such a change can be measured using zeta potential of the surface. As an example, the zeta potentials can change from +30 mV to −40 mV in a first embodiment; from +20 mV to +10 mV in a second embodiment; from −5 mV to −60 mV in a third embodiment; and/or from +30 mV to −10 mV in a fourth embodiment.

Examples of oxyanions include, but are not limited to, bisulfite, meta bisulfite, nitrate, sulfate, metaborate, dithionite, or any combinations thereof, etc. Examples of reducing agents include, but are not limited to, sodium carbonate, sodium nitrate, sodium bisulfite, sodium dithionite, sodium meta bisulfite, any combinations thereof, etc. Of note, sometimes bisulfite is spelled as bisulphite. In one embodiment, the reducing agents is a conjugate base that is reactive to calcite mineral or adsorb on the calcite mineral to cause a charge transfer process, i.e., causing a change in the zeta potential with the addition of the reducing agents.

The amount of reducing agent to be added to the aqueous stream ranges from 150 ppm to 3000 ppm in one embodiment; from 300 ppm to 1500 ppm in a second embodiment; at least 200 ppm in a third embodiment; less than 4500 ppm in a fourth embodiment; from 50 ppm to 1500 ppm in a fifth embodiment; from 50 ppm to 750 ppm in a sixth embodiment; from 80 ppm to 3500 ppm in a seventh embodiment; from 50 ppm to 4500 ppm in an eight embodiment; from 50 ppm to 3500 ppm in a ninth embodiment; less than 5,000 ppm in a tenth embodiment; and/or from 50 ppm to 5000 ppm in an eleventh embodiment. The amount varies depending on the reducing agent(s) added, the concentration of oxyanions inherent in the brine in the formation (formation brine), the concentration of oxyanions in the aqueous stream (e.g., recycled brine water) to be injected into the formation, the temperature of the formation, amongst other factors. In one embodiment with the addition of sodium bisulfite as the reducing agent, the amount of reducing agent added ranges from 50 ppm to 300 ppm, to alter the wettability of the carbonate formation to more water-wet. In another embodiment with the use of sodium meta bisulfite as the reducing agent, the amount of reducing agent ranges from 80 ppm to 400 ppm. With the use of sodium sulfate as the reducing agent, the amount of the reducing agent ranges from 160 ppm to 3000 ppm. With the use of sodium bisulfide as the reducing agent, the amount of reducing agent ranges from 50 ppm to 3500 ppm (e.g., about 1000 ppm).

As rock mineralogy, oil, and brine differ from one formation to another, the optimal reducing agent(s), optimal concentration of reducing agent(s), and their interactions can be evaluated using a Design of Experiments approach. In one embodiment, the Design of Experiments approach is used to screen out various reducing agents/brine compositions by testing their efficacy in changing the contact angles and/or zeta potential. The Design of Experiments approach may provide the minimum number of experiments required to yield an optimal brine composition including concentration and type of the reducing agent(s) in the optimal brine composition). After the Design of Experiments approach has been completed, a brine composition with at least one reducing agent may be selected to enhance recovery of hydrocarbons from the formation. For simplicity, this specification will focus on Design of Experiments as one uncertainty analysis that may be conducted, however, those of ordinary skill in the art will appreciate that the specification (and the appended claims) are not limited to Design of Experiments.

In one embodiment, the effect of reducing agents on the recovery of oil from carbonate rock systems is evaluated by either coreflood tests and/or Amott-Harvey type imbibition tests. The Amott-Harvey type imbibition tests may be conducted as described in API RP 40. The reducing agents are added to de-oxygenated brine for the tests, as the oxygen content is expected to mitigate the effectiveness of the reducing agents.

In one embodiment, Design of Experiments data is collected from coreflood tests conducted using brine with and without reducing agents. In another embodiment, data is also collected from sequential coreflood tests, e.g., a first injection without reducing agents followed by a brine injection with reducing agents may be carried.

In one embodiment, data is collected from coreflood tests under any of the conditions: a) a first injection with additives (e.g., reducing agents) followed by a brine injection with surfactants; b) tests with brine injection containing a combination of additives (e.g., reducing agents); c) brine injection with different concentration of additives (e.g., reducing agents), e.g., from 10 ppm to 10,000 ppm; d) brine injection with different additives (e.g., reducing agents) at different concentrations and at different brine temperatures/reservoir conditions; e) tests with brine compositions simulating formation water from different rock mineralogy with and without additives (e.g., reducing agents); f) tests with different calcareous mineral substrates that are wettability restored; and g) tests with the mineral substrates being treated or soaked with brine with additives (e.g., reducing agents) for different periods of time, e.g., 1 day to 2 weeks.

In one embodiment, zeta potential data is also collected as part of the Design of Experiments. The zeta potential data is collected to see if the slope on a graph between zeta potential and concentration is negative, e.g., decreasing zeta potentials with increasing concentrations. In another embodiment, x-ray photoelectron spectroscopy (XPS) results are also collected. For example, if the XPS results show >30% reduction of hydrogen coverage at elevated temperatures, e.g., greater than 70° C. From the Design of Experiments, interactions of the various additives (e.g., reducing agents) with brine compositions, formation conditions, etc., can be determined and correlated, e.g., if the tests show positive results in terms of zeta potential, XPS results, de-wetting of the oil, negative wetting, water-wetness, etc. The database/ correlations can be used in determining the additives (e.g., reducing agents) to be added to brine compositions to change formation wettability.

As described herein, a Design of Experiments method may be used to screen brine additives (e.g., reducing agents, cations, anions, etc.)/compositions using contact angle and zeta potential methods. The screened brines are used to perform either core floods or Amott-Harvey Wettability studies. One embodiment to select a brine composition to be injected into a formation to alter wettability at a surface of the formation towards more water-wet may include: providing a plurality of substrates representative of the formation; providing a plurality of brine compositions; providing a plurality of reducing agents characterized as yielding oxy-anions when added to the aqueous stream, wherein the oxyanions are selected from carbonate ($CO_3^{2-}$), nitrate ($NO_3^-$), metabisulfite ($[S_2O_5]^{2-}$), bisulfite ($HSO_3^-$), dithionite ($[S_2O_4]^{2-}$), sulfate ($SO_4^{2-}$), or any combination thereof; conducting a Design of Experiments using various combinations of the substrates, the brine compositions, and the reducing agents; correlating results from the Design of Experiments to determine interactions between the reducing agents, the brine compositions, and concentration of the reducing agents with wettability altering characteristics; and using the correlated results from the Design of Experiments to select a brine composition with at least one reducing agent to inject into the formation. wherein the Design of Experiments comprises sessile drop tests, contact angle tests, spreading coefficient tests, zeta potential tests, soaking at least some of the plurality of substrates in some of the brine compositions for predetermined periods of times before adding any reducing agent to these brine compositions, adding a droplet of oil to at least one soaked substrate, adding a predetermined amount of a particular reducing agent to a particular brine composition and analyzing changes in wettability of particular substrate, or any combination thereof. The Design of Experiments comprises sessile drop tests, contact angle tests, spreading coefficient tests, zeta potential tests, soaking at least some of the plurality of substrates in some of the brine compositions for predetermined periods of times before adding any reducing agent to these brine compositions, adding a droplet of oil to at least one soaked substrate, adding a predetermined amount of a particular reducing agent to a particular brine composition and analyzing changes in wettability of particular substrate, or any combination thereof.

Methods to Engineer Compositions to Change Formation Wettability:

As rock mineralogy, hydrocarbon, and brine compositions differ from one formation to another. The steps to engineer the brine chemistry in one embodiment are as follows, although not all steps are required and not necessarily in the order as listed Obtain characteristics of the formation, for example, rock mineralogy (e.g., Qualitative X-ray Diffraction to yield the composition of the rock, i.e. the wt. % of dolomite, calcite, anhydrite, clay, etc.), Optionally obtain characteristics of the formation such as pore geometry, dimensions, etc.

Obtain characteristics of the brine of the formation, for example, compositions of the anions and cations in the brine (sodium, calcium, magnesium, chloride, etc.) and the oxyanions present such as bisulfite, metabisulfite, nitrate, sulfate, metaborate, etc.

Obtain characteristics of the hydrocarbons of the formation, for example, e.g., crude oil composition, acid number, base number, etc.

Obtain characteristics of the aqueous stream (de-aerated and de-oxygenated aqueous stream or brine composition) without additives, e.g., sea water, fresh water, recycled produced brine, etc., including acid number, pH, composition (e.g., concentration of anions and cations such as sodium, calcium, chloride, etc. and concentration of oxyanions), any other chemicals added for corrosion inhibition, oxygen reduction, emulsion control, etc.

Identify optional additives (e.g. anions, cations, surfactants, polymers, etc.) to add to the aqueous stream, e.g., surfactants for changing interfacial tension (IFT), surfactants for generation of foam, polymers for increasing viscosity, etc.

Provide a database correlating interactions of additives selected from reducing agents with characteristics of the formation, the aqueous stream, and the optional additives (e.g. anions, cations, surfactants, polymers, etc.)

The database may correlate interactions of a plurality of reducing agents with the characteristics of the formation, the characteristics of the brine, and the characteristics of the hydrocarbons. The database may further contain interactions of the plurality of the reducing agents with zeta potential data of the formation. The database may further contain interactions of the plurality of the reducing agents with contact angle data of the formation.

Determine the additive (e.g., reducing agent) and concentration to be added to the aqueous stream to alter the wettability of the formation.

The above method for selecting an additive or a plurality of additives can be employed to engineer a brine composition for enhanced oil recovery in carbonate formations, particularly formations comprising calcareous and dolomitic mineral rock having an inherently less negative charge at the surface (i.e., a reduction in surface charge value), and particularly for formations that have gone through the primary recovery phase (e.g., the primary recovery phase typically relies on pressure for hydrocarbon recovery). The additive (e.g., reducing agent) is expected to have an impact on the wettability, which can be demonstrated by methods known in the art, e.g., contact angle, spreading coefficient, or adhesion properties with soak period using the sessile drop technique. A positive test for wettability alteration is indicated by a contact angle shift from >90° to <90°. This shift may occur due to either a negative spreading coefficient, or a change in adhesion properties after a soak period. Another positive test for wettability alteration is the absence of adhesion during adhesion testing.

The impact of an additive (e.g., reducing agent) on surface concentration of hydrocarbon at different temperatures can be evaluated using XPS technique. The substrate, covered with adsorbed hydrocarbon, is subjected to soak treatment at 33° C. and at higher temperatures, typically reservoir conditions, to determine the low and high temperature behavior. The XPS test result at low temperature is used to confirm the effect due to surface charge transfer process when hydrocarbon coverage on the calcite surface exists. At higher temperature, the surface hydrocarbon coverage is reduced due to desorption.

Other Factors for Engineering Wettability:

It is to be noted that the application of these additives (e.g., reducing agent) for wettability alteration and recovery from carbonate rocks systems may also be implemented with appropriate pH or alkalinity control. The increase in pH towards more neutral or alkaline is only expected to support the wettability alteration process. The increase in pH may be achieved by maintaining appropriate levels of bicarbonate/carbonate or hydroxide anion concentrations. This can in turn be achieved by adding alkali metal salts of bicarbonate/carbonate or hydroxide.

Benefits-Reducing Surfactant Usage/Adsorption:

In typical enhanced oil recovery operations with surfactant formulations, there is an issue of surfactant retention in carbonate formations, which can be severe in the case of anionic surfactants with a greater tendency to get adsorbed to the surface of the rock grains. The adsorption impedes the effectiveness of surfactant. To reduce the surfactant adsorption, the pH of the formation brine is raised with the addition of additives such as sodium hydroxide or sodium carbonate, which leads to precipitation problems of hydroxides of the calcium cations in abundant supply in the formation.

By engineering the brine composition to alter the wettability of the surfaces of the formation, only a fraction of the normal surfactants typically needed for water/polymer flooding is required, thus obviating the surfactant adsorption problem. In one embodiment, the amount of required surfactants is reduced at least 10% with a treatment (e.g., pre-flush or pre-treatment) of the formation with the selected additives (e.g. reducing agent). In another embodiment, the reduction in required surfactants is at least 25%.

In addition to a reduction in the amount of required surfactants, the selected additives (e.g., reducing agent) in one embodiment also reduce surfactant adsorption by altering electrochemical potential and therefore surface charge, obviating the need for alkali addition to elevate the pH of the injected brine composition. Lastly, the selected additives (e.g., reducing agent) can be used in an aqueous stream to "flush" the formation and change its wettability characteristics prior to the injection of an aqueous stream with a reduced concentration of surfactants (compared to an EOR stream for a method without a flushing step).

Measuring Wettability:

In-situ formation wettability measurements can be made by performing a down-hole testing of imbibition rates. These measurements can be taken by a number of analytical tools. In some embodiments, the analytical tools may include, but are not limited to, NMR (can measure relaxation and diffusion), electrical resistivity tools (e.g., electrical array tools), ultrasonic tools, and various nuclear tools that can monitor, for example, sigma-capture cross section or carbon/oxygen ratios. These analytical tools can image or detect fluid front, measure saturation of fluid(s), and/or otherwise monitor movement of fluid front, which, in turn, can be used to determine wettability. In some embodiments, wettability measurements can be made in real-time, semi real-time, and/or post-treatment (e.g., after a hydraulic fracturing treatment).

Imbibition rates can be determined by measuring movement of the front. Wettability may be qualitatively assessed (e.g., more water-wet, mixed-wet or more oil-wet) based on the imbibition rate in comparison to a model rock type. Slope of the imbibition rate curve can be compared to imbibition rates of a model rock, e.g., Berea sandstone for a sandstone formation or an outcrop carbonate for a carbonate formation. Similarly, other imaging techniques that can be used downhole can provide imbibition rates. During imbibition, the aqueous stream will generally take the path of least resistance (e.g., along permeable beds constrained by impermeable beds) and also depend on the type of injection. In some cases, the aqueous stream can flow radially or start in a single direction and slowly spread out.

One method for measuring the wettability in the lab is contact angle, to measure the angle which the tangent to the water-oil interface makes with a smooth mineral surface. In the method, an oil droplet is submerged under brine and held against a flat, optically smooth, mineral surface. The angle so measured is a function of the surface chemistry of the formation, brine chemistry, oil chemistry, and the oil-brine interfacial properties. When the measured angle through the surrounding brine phase is less than 90°, then the mineral surface is considered to be mildly water-wet to strongly water-wet. When the angle is greater than 90°, the mineral surface is considered to be mildly oil-wet to strongly oil-wet.

Another technique is measuring the spreading coefficient, which is a function of the surface and interfacial energies of the mineral-brine, mineral-oil interface, and the oil-brine interface. The spreading coefficient is generally positive for fluids that spread on a solid surface, and negative for fluids that contracts or "balls" up. A third approach is via adhesion testing, where a drop of oil held at the tip of a needle is contacted with a solid surface to qualitatively assess whether the drop adheres to the solid surface, and whether the drop of oil detaches itself. Yet another approach is with the Amott-Harvey wettability test, with an Amott water index $I_w=1$ to denote a strongly water-wet condition.

The effectiveness of the reducing agents to alter wettability to cause the formation to desorb the adsorbed components of hydrocarbons, e.g., crude oil, can be measured by studying the surface of the substrate using X-ray photoelectron spectroscopy ("XPS"), where XPS measurements indicate the percent of the surface covered by the hydrocarbon components of the crude oil.

EXAMPLE

The following illustrative examples are intended to be non-limiting.

Example 1

Figure 1B:
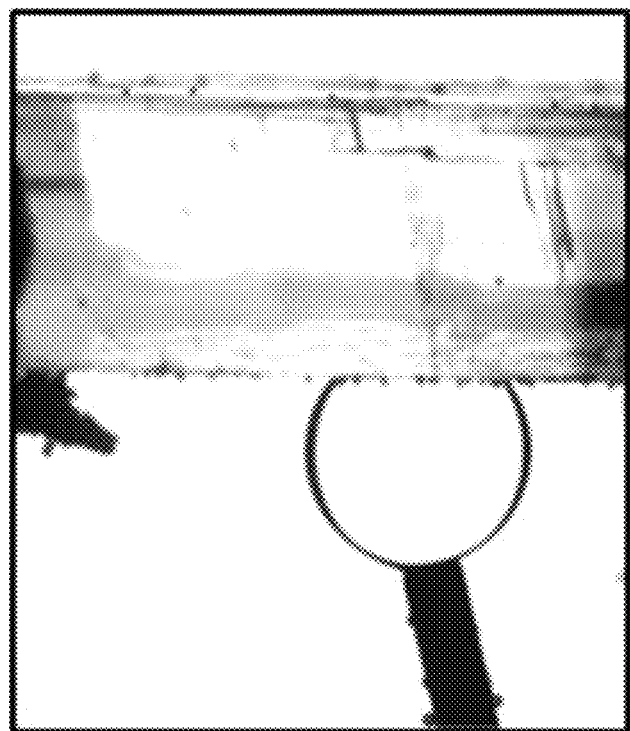

As shown in FIGS. 1A-1B, a droplet of an alkane (proxy for the hydrocarbon) is deposited on the surface of a carbonate mineral with an intervening brine layer. The intervening layer thickness is reduced with time as the droplet presses against the mineral surface. The forces that are involved are commonly known as the DLVO components (for Derjaguin, Landau, Verwey and Overbeek) for the electrostatic force that is a result of electrical charge on the interfaces—oil-brine and brine-rock. The measurement of the electric surface potential (zeta) can give information about the surface charge and its variation with respect to added components. The extent of the spread of the alkane is indicative of the wettability as is the contact angle. The contact angle of the oil drop through the brine phase is less than 90 degrees which is indicative of the water-wetting tendency.

Example 2

Figure 2A:
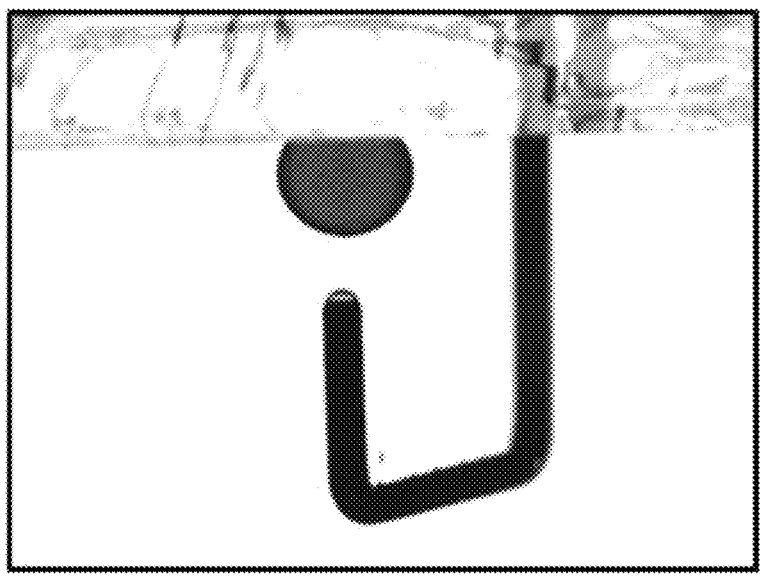
FIGS. 2A, 2B, and 2C are photographs illustrating a single drop of crude oil with small quantities of acidic and basic compounds on a carbonate mineral.
Figure 2B:
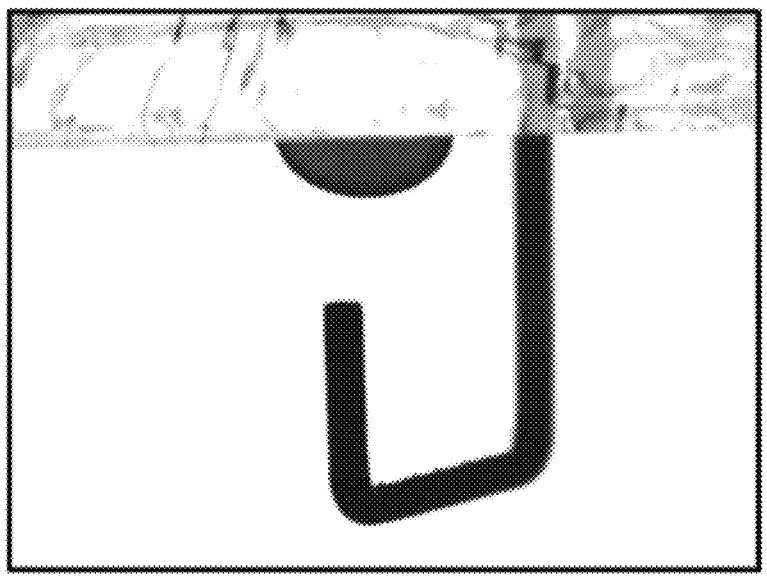
Figure 2C:
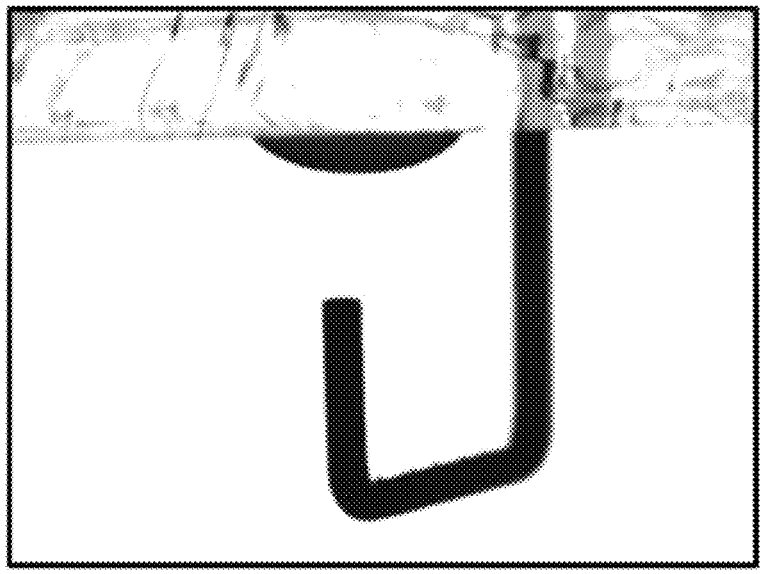

As shown in FIGS. 2A-2C, a single drop of crude oil (with small quantities of acidic and basic compounds) is placed on a carbonate mineral. The spread in the droplet of the oil occurs spontaneously on the substrate, which suggests a favorable interaction between the surface and the oil droplet. However, once the oil droplet attaches itself to the substrate mineral surface, surfactants from the oil migrate and react with the surface. This cause the oil droplet to stay spread on the mineral surface. This indicates a preferentially oil-wet surface.

Example 3—Control Sample

Figure 3A:
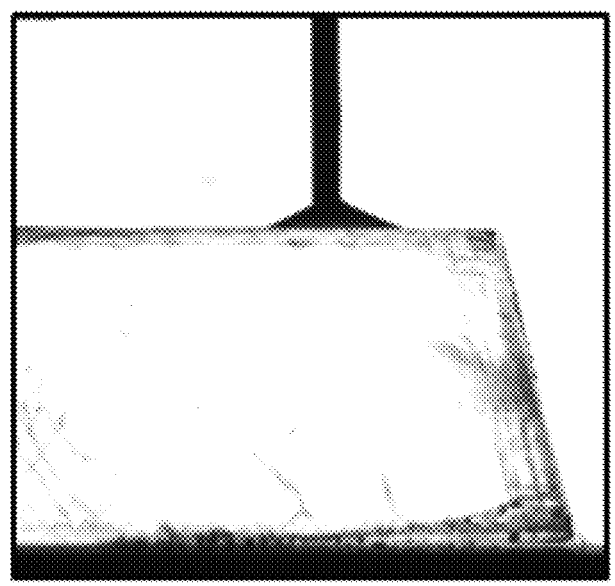
FIGS. 3A, 3B, and 3C are photographs illustrating a sessile oil droplet absent of any additive (e.g. reducing agent) on aged calcite substrate.
Figure 3B:
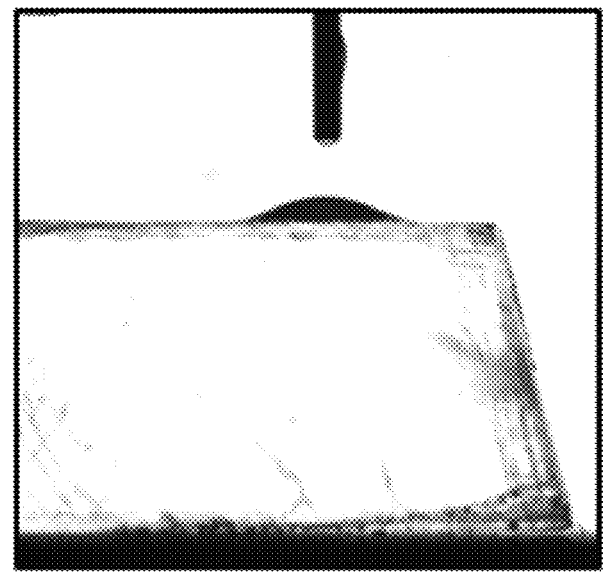
Figure 3C:
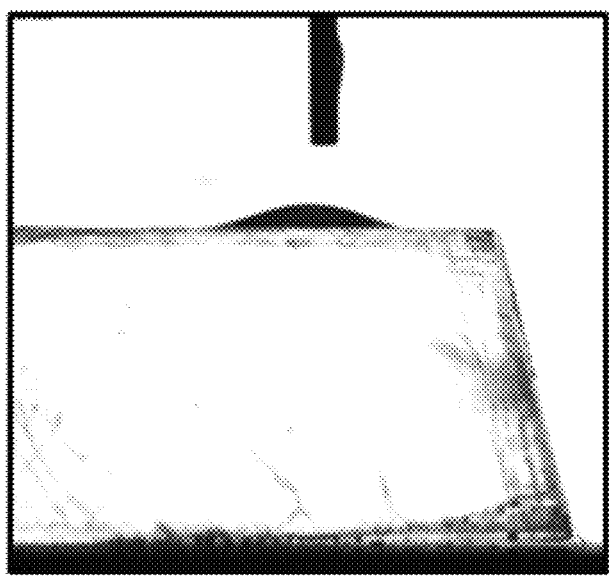

As shown in FIGS. 3A-3C, an oil droplet (a sessile drop) absent of any additive (e.g., reducing agent) is placed on aged calcite substrate. The oil droplet is spreading on the substrate surface and completely wetting it. The droplet is only large enough so flotation does not occur.

Example 4

In this example and as illustrated in FIGS. 4A-4E, sodium bisulfite is used to alter wettability in a calcium carbonate mineral surface. The sodium bisulfite solution is prepared with a de-aerated brine to prevent oxidation of the additive (e.g., reducing agent). The addition was made at a temperature of 33° C. to the surrounding brine during a measurement of contact angle on calcite surface containing 20% to 70% C atoms as hydrocarbon. The initial contact angle is approximately 170° on the aged substrate (which indicates a strongly oil-wet surface). After addition of the reducing agent, sodium bisulfite, the surface wettability changes towards more water-wet. The final contact angle is approximately 90° on the aged substrate (which is neutral-wet). The change in contact angle takes place within 10 seconds and the concentration of the sodium bisulfite in the surrounding brine phase is 80 ppm. The addition of sodium bisulfite also leads to poor adhesion on the carbonate surface in addition to negative spreading coefficient of oil on the carbonate mineral surface.

Figure 4A:
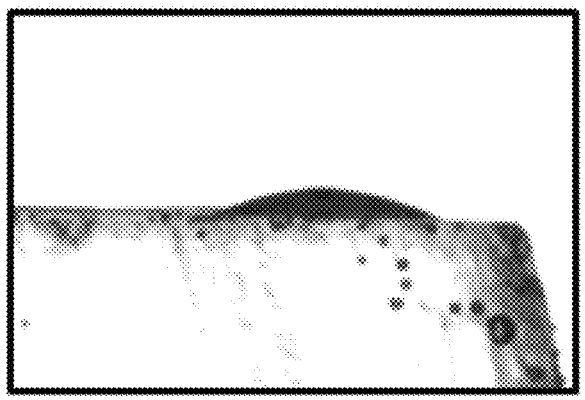
FIGS. 4A, 4B, 4C, 4D, and 4E are photographs illustrating the effect of sodium bisulfite on wettability on a calcium carbonate mineral surface.
Figure 4D:
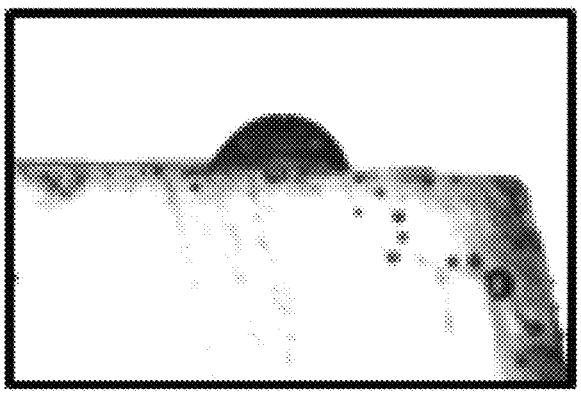
Figure 4B:
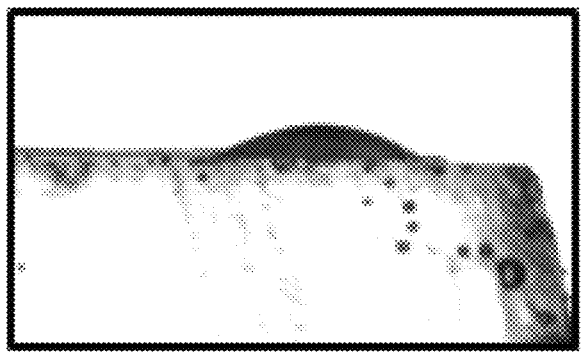
Figure 4E:
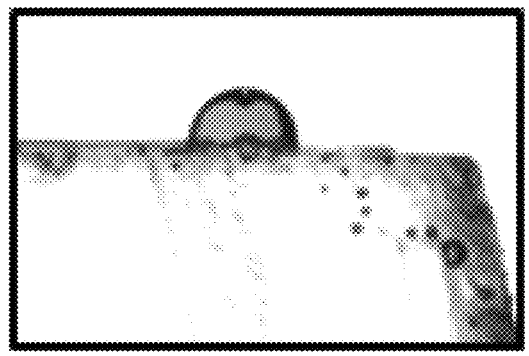
Figure 4C:
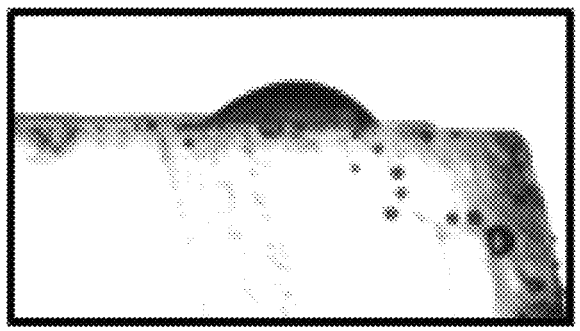

FIG. 4A shows the sessile drop on the flat calcite substrate. The oil droplet (1 ml volume) spreads spontaneously. When sodium bisulfite is added (to 80 ppm level), the oil droplet spontaneously balls up and the oil-water-mineral contact line recedes as illustrated in FIGS. 4B-4E. As shown, the spreading coefficient of oil on calcite surface turns to more negative values (with a reduction in spreading coefficient value). The reversal in spreading coefficient takes place over ~10 seconds. In short, the oil droplet spreading (wetting) is significantly decreased and the system moves towards more water-wet by the addition of small quantities of sodium bisulfite (80 ppm in this example).

Example 5

Figure 5A:
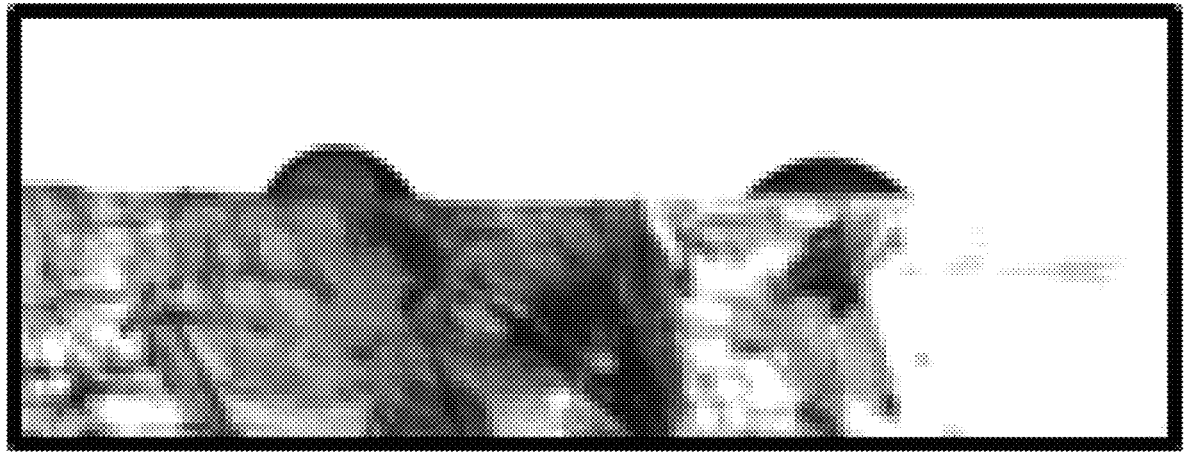
FIGS. 5A-5B are photographs illustrating the effect of sodium metabisulfite on wettability on a calcium carbonate mineral surface.
Figure 5B:

In this example and as illustrated in FIGS. 5A-5B, sodium metabisulfite prepared in de-aerated brine at 33° C. is used. In FIG. 5A, the initial contact angle is approximately 140° on unaged calcite surface and approximately 170° on aged calcite surface. In FIG. 5B, the final contact angle is approximately 90° on unaged calcite surface and 110° on aged calcite surface. The changes in contact angle take place within 30 seconds after achieving the required concentration in the case of unaged substrate. The concentration of the sodium metabisulfite salt in the surrounding brine phase required to alter the wettability of unaged calcite surface is 80 ppm. The concentration required to cause wettability shift on aged calcite is 360 ppm. As shown in the FIGS. 5A-5B, when sodium metabisulfite is added, the oil droplet spontaneously balls up and the oil-water-mineral contact line recedes. In short, in FIG. 5A, oil is spreading or wetting the substrate surface without the additive (e.g., reducing agent), while in FIG. 5B, the spreading or wetting of the oil is decreased significantly (i.e., the system has moved towards more water wetting) with the reducing agent (80 ppm and 360 ppm respectively), Example 6

Figure 6A:
FIGS. 6A-6B are photographs illustrating the effect of sodium sulfate on wettability on a calcium carbonate mineral surface.
Figure 6B:
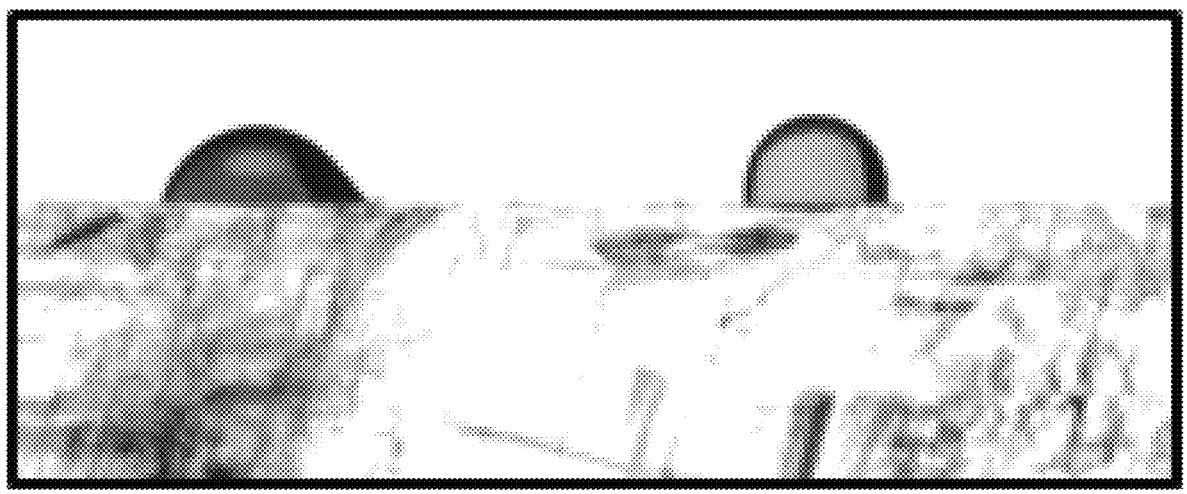

In this example and as illustrated in FIGS. 6A-6B, sodium sulfate at concentration at 33° C. is used. Sodium sulfate at 3000 ppm changes the contact angle on unaged calcite from >90° to <90° over 30 seconds after achieving the required concentration. The initial contact angle is ~140° and the final contact angle is ~45° on unaged calcite substrate. The concentration of sodium sulfate required to cause poor adhesion on unaged calcite is 3000 ppm. As shown in the FIGS. 6A-6B, when sodium sulfate is added, the oil droplet spontaneously balls up and the oil-water-mineral contact line recedes. For example, after addition of sodium sulfate to the extent of 3000 ppm, the adhesion properties were affected and the crude oil showed less oil-wet and more water-wet condition. Addition of sodium sulfate up to 3000 ppm caused retraction of the oil droplets or induced a negative spreading coefficient. In short, in FIG. 6A, oil is spreading or wetting the substrate surface without the additive (e.g., reducing agent), while in FIG. 6B, the spreading or wetting of the oil is decreased significantly (i.e., the system has moved towards more water wetting) with 3000 ppm of the additive (e.g., reducing agent).

Example 7

Figure 7A:
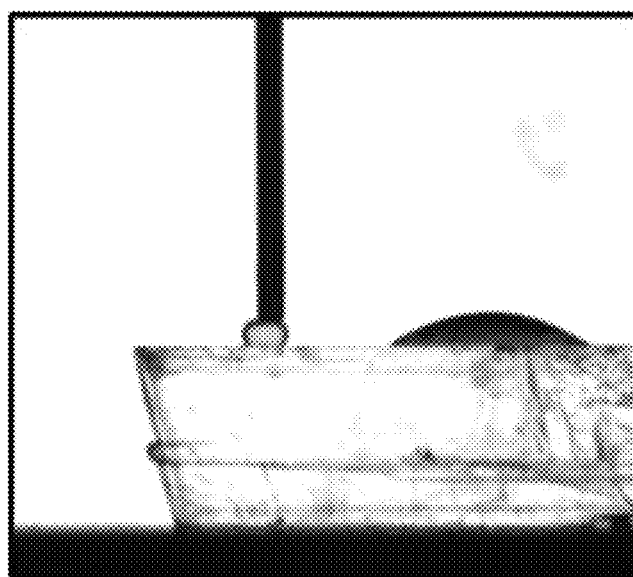
FIGS. 7A-7C are photographs illustrating the effect of sodium nitrate on wettability on a calcium carbonate mineral surface.
Figure 7B:
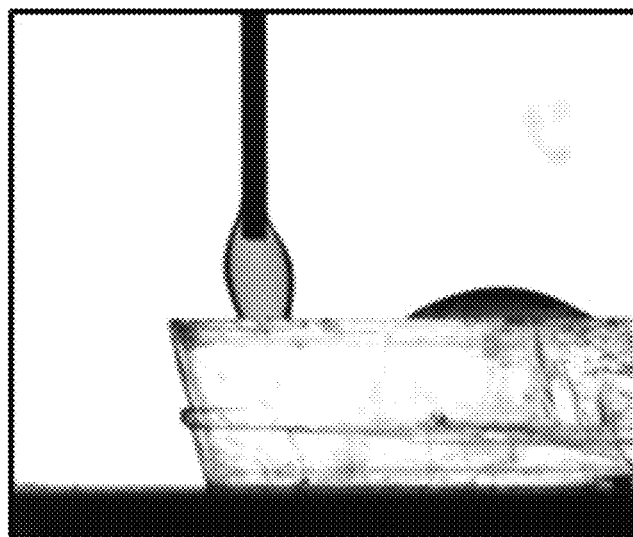
Figure 7C:
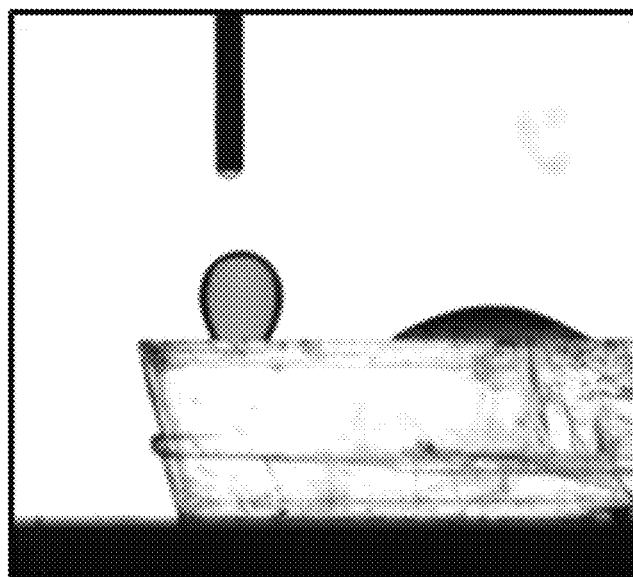

As illustrated in FIGS. 7A-7C, sodium nitrate at a concentration of 1000 ppm at 33° C. is used on a calcite surface both aged and unaged calcite substrates, leading to water-wet condition. The action of wettability change, observed through adhesion testing, takes place over time with over 12 hours of soak in the brine. The initial contact angle is approximately 140° on unaged calcite surface and approximately 170° on aged calcite surface. The final contact angle is approximately 60° through water phase on aged surface while the unaged surface does not display any adherence at all.

Example 8

Example 7 is repeated and adhesion behavior after addition of sodium nitrate is found to be water-wet even at a sodium nitrate concentration of 450 ppm.

Example 9

Figure 8A:
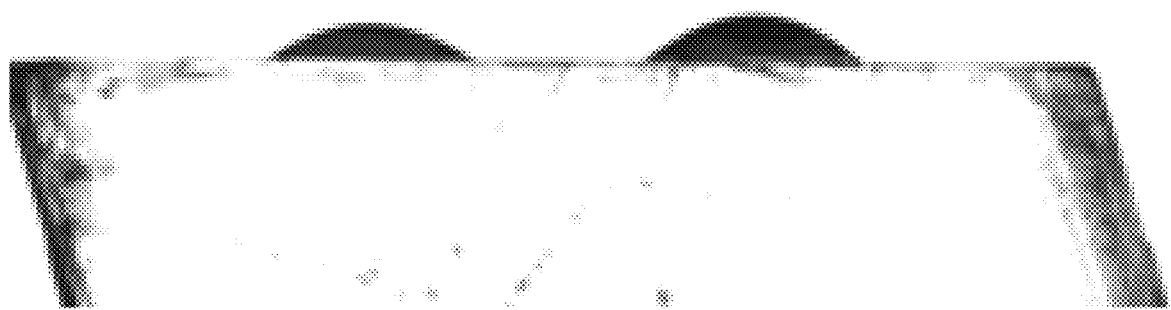
FIGS. 8A-8B are photographs illustrating the effect of sodium dithionite on wettability on a calcium carbonate mineral surface.
Figure 8B:

In this example and as illustrated in FIGS. 8A-8B, aged calcite substrate is dewetted in formation brine dosed with sodium dithionite at 550 ppm. The sodium dithionite is prepared with a de-aerated brine to prevent oxidation of the additive (e.g., reducing agent). In FIG. 8A, the oil sessile drop (1 ml volume) on the flat calcite substrate spreads spontaneously. When sodium dithionite is added, the oil droplet spontaneously balls up and the oil-water-mineral contact line recedes as shown in FIG. 8B. The dewetting takes place over a period of 4 hours approximately at room conditions.

Surface hydrocarbon coverage is measured using XPS. The results show that freshly cleaved unaged calcite crystal used has a surface coverage of 23.5+ or –6 atoms percent of Carbon as hydrocarbon. Aged calcite mineral crystal samples show an average of 66+ or –8 atoms percent of Carbon as hydrocarbon. In short, in FIG. 8A, oil is spreading or wetting the substrate surface without the additive (e.g., reducing agent), while in FIG. 8B, the spreading or wetting of the oil is decreased significantly (i.e., the system has moved towards more water wetting) with the reducing agent (550 ppm).

Example 10

Calcite mineral plates are immersed and soaked at 25° C. for 1 week in brines containing sodium nitrate (X1 brine), sodium metaborate (X2 brine), and sodium sulfate (X3 brine) then measured using XPS. Results show surface coverages of 73+–7%, 64+–5%, and 59+–12% of Carbon atoms as hydrocarbon respectively for X1, X2, and X3 brine, which is almost the same as that of untreated brines.

Example 11

Example 10 is repeated except that the soaking is at 70° C. The surface coverage in the samples treated with the brines at 70° C. is found to be significantly lower (31+–4 percent Carbon as hydrocarbon) than at room temperature. The elevated temperatures do not cause any dissolution and thus positively identifies the effect of additives (e.g., reducing agent) in desorbing the hydrocarbons.

Example 12

Figure 9:
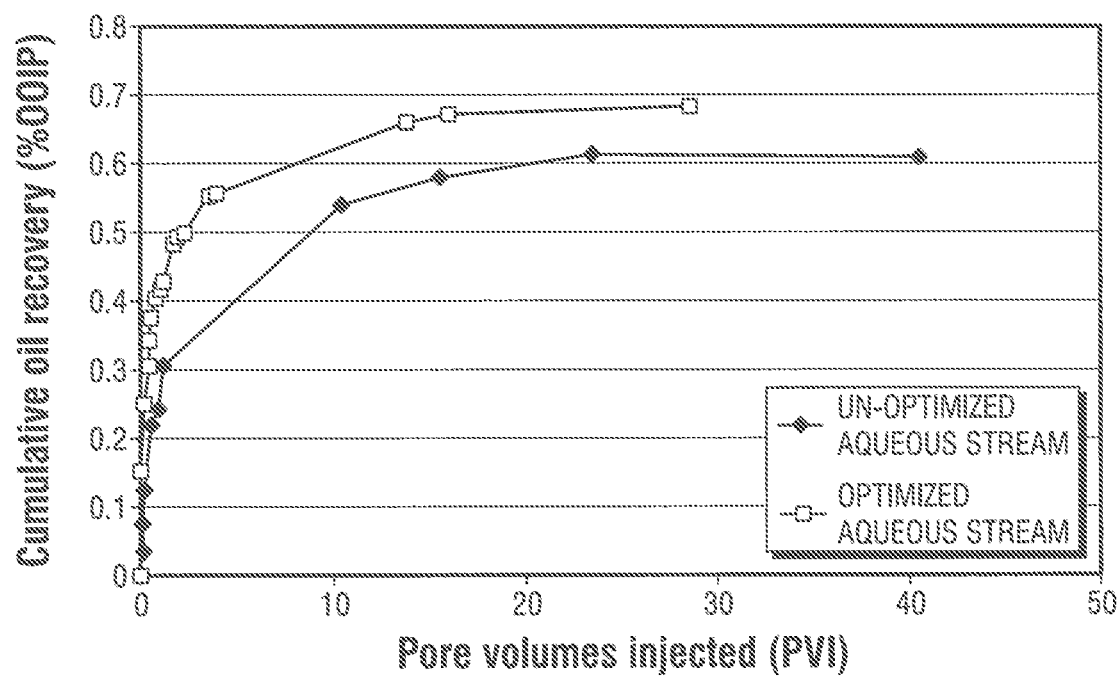
FIG. 9 is a graph illustrating the use of sodium sulfate as a reducing agent to enhance oil recovery from cores by injection of an optimized aqueous stream.

As shown in FIG. 9, corefloods are performed on a restored Dolomitic core. The restoration process includes ageing the core in oil under similar conditions of oil saturations as would exist in an oil bearing formation for 4 weeks. Subsequently, the core is subjected to injection of an aqueous stream to mimic the oil recovery in the formation. Two coreflood experiments are performed on core contained in a vertical coreholder. In one coreflood experiment, the experiment included injecting an un-optimized aqueous stream, while the second is a coreflood experiment with optimized (engineered) aqueous stream containing at least one reducing agent (e.g., sodium sulfate). When the optimized (engineered) aqueous stream is injected in the core, the oil recovery is increased from 61% of original oil in place (OOIP) to 68% of OOIP (which is ~11.5% improvement in the oil recovery).

Example 13

Figure 10:
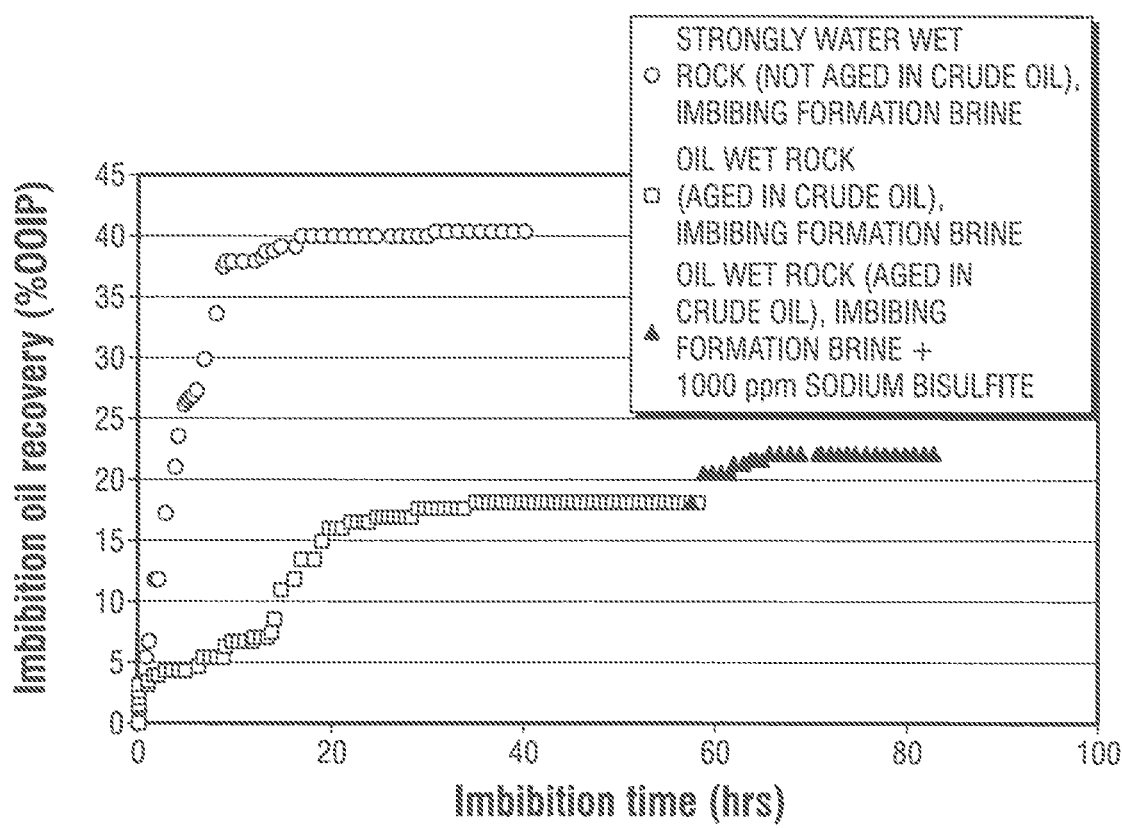
FIG. 10 is a graph illustrating the enhanced recovery of oil with use of sodium bisulfite as a tertiary oil recovery.

FIG. 10 is a graph illustrating the enhanced recovery of oil with use of sodium bisulfate as a tertiary oil recovery. The circles represent the oil recovery curve from a strongly water-wet core that is unaged with crude oil using an aqueous stream of the brine from the formation. The circles represent the hypothetical best oil recovery that can be achieved from the formation, because actual formation is not strongly water-wet. The squares represent oil recovery from the formation to a better extent. The squares show oil recovery from a core saturated with formation brine and crude oil and aged to restore wettability to less water-wet conditions. Under these conditions (which are closer to reservoir conditions compared to the circles), one can recover only about 18% of oil in place with a regular (un-optimized) aqueous stream. After the plateau in oil recovery with the un-optimized aqueous stream is reached, adding 1000 ppm of sodium bisulfite, as the reducing agent, to an aqueous stream results in alteration of the wettability towards more water-wet as illustrated by the data triangles, which increases the recovery to about 22% of OOIP (or 22% improvement over the oil recovery of square data).

Example 14

Figure 11:
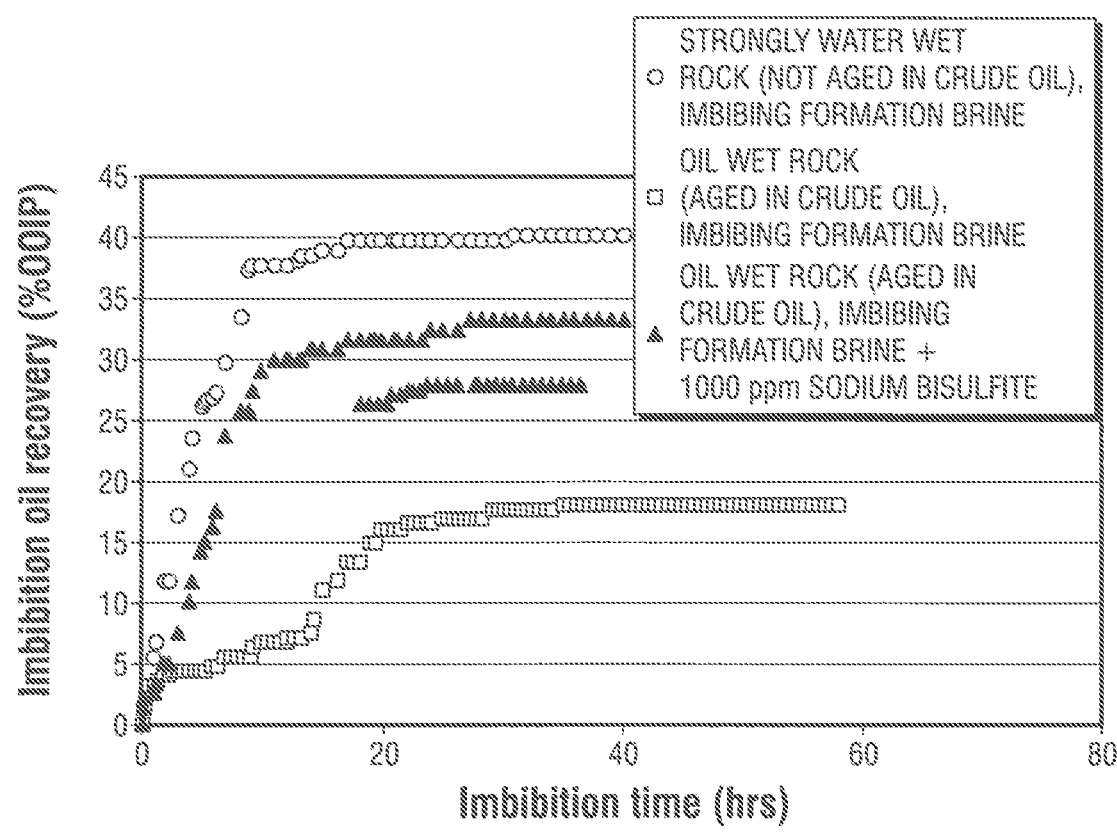
FIG. 11 is a graph illustrating the enhanced recovery of oil with use of sodium bisulfite as a secondary oil recovery.

FIG. 11 is a graph illustrating the enhanced recovery of oil with use of sodium bisulfite as a secondary oil recovery. The circles represent the oil recovery curve from a strongly water-wet core that is unaged with crude oil using an aqueous stream of the brine from the formation. The circles represent the hypothetical best oil recovery that can be achieved from the formation, because actual formation is not strongly water-wet. The squares represent oil recovery from the formation to a better extent. The squares show oil recovery from a core saturated with formation brine and crude oil and aged to restore wettability to less water-wet conditions. Under these conditions (which are closer to reservoir conditions compared to the circles), one can recover only about 18% of oil in place with a regular (un-optimized) aqueous stream. However, adding 1000 ppm of sodium bisulfite, as the reducing agent, to the aqueous stream from the beginning of the process, results in alteration of the wettability towards more water-wet (closer to the circle data). This alteration increases the oil recovery to 33% of OOIP (or 83% improvement over the square data).

Example 15

Figure 12:
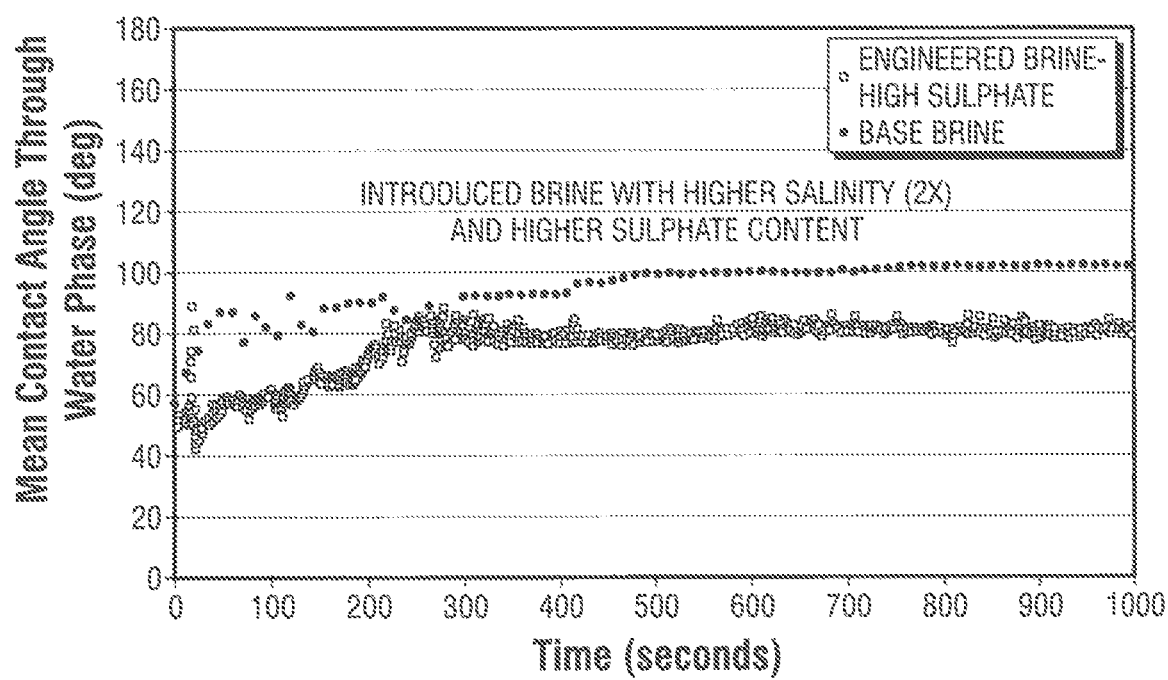
FIG. 12 is a graph illustrating the shift in the contact angle for the example with the use of sodium sulfate.

FIG. 12 is a graph illustrating measurements of wettability by using the contact angle method of FIG. 6. FIG. 12 shows a shift in contact angle from slightly oil-wet conditions (contact angle greater than 90 degrees) to a slightly water-wet condition (contact angle less than 90 degrees). Prior to the exposure to a brine containing sodium sulfate, the wettability is slightly oil wet (100°). However, subsequent to the exposure to sodium sulfate, the wettability is slightly water-wet (80°). Although the shift in wettability is small in magnitude, the impact is significant because of the impact on capillary pressure. The capillary pressure undergoes a change from negative, when oil-wet (>100°), to positive at water-wet conditions (<90°).

Mobility Control Agent:

In some embodiments, at least one mobility control agent may be used in addition to an additive (e.g., reducing agent) discussed hereinabove. For example, in some embodiments, at least one mobility control agent may be used in addition to a reducing agent and/or a surfactant discussed hereinabove. The mobility control agent may be a foam or a polymer. For example, in some embodiments, a mobility control method can be used to enhance the oil recovery from the formation (e.g., fractured formation) by increasing the viscosity of the brine (aqueous stream): a) in-situ generation of foam by co-injection or alternate injection of a surfactant and a gas; orb) injection of 50 ppm to 5000 ppm of a brine soluble polymer with the injected aqueous stream. In some embodiments, the quantity of the polymer may be less than 3500 ppm on one embodiment; less than 1500 ppm in a second embodiment; and/or from 50 ppm to 1500 ppm in a third embodiment. The polymer may be similar to hydrolyzed polyacrylamide (HPAM).

Regarding the foam, the mobility control agent may be formed by co-injection of a gas phase with the aqueous stream containing a surfactant (or plurality of surfactants and other chemicals), or alternate injection of aqueous stream containing a surfactant (or plurality of surfactants and other chemicals) and a gas (e.g., nitrogen), each of which may lead to generation of the foam in the formation that may increase the viscosity of the aqueous stream. In another embodiment, the mobility control agent may be formed by co-injection of the aqueous stream with liquid $CO_2$ containing a surfactant (or plurality of surfactants and other chemicals), or alternate injection of the aqueous stream and liquid $CO_2$ containing a surfactant (or plurality of surfactants and other chemicals), all of which may lead to generation of foam in the formation that increases viscosity of the aqueous stream. In some embodiments, the quantity of the surfactant for the foam may be in the range of 0.25 vol. % to 4.0 vol. % in one embodiment; 0.25 vol. % to 2.0 vol. % in another embodiment; 0.5 vol. % to 2.0 vol. % in another embodiment; and/or 1.0 vol. % to 3.0 vol. % in another embodiment. In some embodiments, the quantity of the nitrogen for the foam that is co-injected with a brine may be in the range of 10 vol. % to 70 vol. % in one embodiment; at least 10 vol. % in another embodiment; less than 80 vol. % in another embodiment; at least 50 vol. % in another embodiment; 40 vol. % to 70 vol. % in another embodiment. The foam may be a nitrogen and surfactant mixture.

Injection Techniques:

An aqueous stream may be an "optimized aqueous stream" when it includes one or more reducing agents. In one embodiment, an optimized aqueous stream may be a brine with at least one reducing agent. In one embodiment, an optimized aqueous stream may be a brine with at least one reducing agent and at least one surfactant (and the brine itself may or may not have other components). In one embodiment, an optimized aqueous stream may be a brine with at least one reducing agent and at least one mobility control agent (and the brine itself may or may not have other components). In one embodiment, an optimized aqueous stream may be a brine with at least one reducing agent, at least one surfactant, and at least one mobility control agent (and the brine itself may or may not have other components). In one embodiment, an optimized aqueous stream may be a brine with an additive, and the additive includes at least one reducing agent (and the brine itself may or may not have other components), and so on. In some embodiments, the reducing agent, the surfactant, and the mobility control agent may each be in different aqueous streams or at least two (e.g., all three) may be in a single aqueous stream.

In some embodiments, an un-optimized aqueous stream (e.g., brine without a reducing agent) may be injected for a certain period of time before switching to the optimized aqueous stream (e.g., brine with a reducing agent), as in FIG. 10 for example. In some embodiments, a particular formation can be waterflooded with the un-optimized aqueous stream for a period of time before switching to the optimized aqueous stream. In some embodiments, injection may alternate between optimized aqueous stream and un-optimized aqueous stream to reduce cost. Alternatively, in some embodiments, the optimized aqueous stream may be used from the start of the enhanced oil recovery process, as in FIG. 11 for example.

In short, there are many wants to implement the embodiments herein. For example, a surfactant, a mobility control agent, or any combination thereof may be provided to an aqueous stream having the reducing agent (i.e., optimized aqueous stream). The aqueous stream having the reducing agent and the surfactant, the mobility control agent, or any combination thereof may be injected into the formation after an aqueous stream without the reducing agent is injected into the formation. In another example, a second aqueous stream comprising surfactant, mobility control agent, the reducing agent, or a combination thereof may be injected into the formation after injection of the aqueous stream with the reducing agent (i.e., optimized aqueous stream). In another example, the aqueous stream with the reducing agent (i.e., optimized aqueous stream) is injected into the formation after an aqueous stream without the reducing agent is injected into the formation. In another example, injecting the aqueous stream with the reducing agent (i.e., optimized aqueous stream) into the formation includes alternating injection of an aqueous stream without the reducing agent and the aqueous stream with the reducing agent (i.e., optimized aqueous stream). In another example, an ionic composition of the aqueous stream with the reducing agent may be changed.

The compositions and methods of the appended claims are not limited in scope by the specific compositions and methods described herein, which are intended as illustrations of a few aspects of the claims. Any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The invention claimed is:

1. A method to select a brine composition to be injected into a formation to alter wettability at a surface of the formation to enhance recovery of hydrocarbons from the formation, the method comprising:
   providing a plurality of substrates representative of a formation;
   providing a plurality of brine compositions;
   providing a plurality of reducing agents characterized as yielding oxyanions when added to an aqueous stream;

selecting a brine composition with at least one reducing agent based on interactions between the plurality of substrates, the plurality of brine compositions, and the plurality of reducing agents, wherein selecting the brine composition with the at least one reducing agent comprises:
  conducting an uncertainty analysis using various combinations of the plurality of the substrates, the plurality of the brine compositions, and the plurality of the reducing agents;
  correlating results from the uncertainty analysis to determine interactions between the plurality of the reducing agents, the plurality of the brine compositions, and concentrations of the plurality of the reducing agents with wettability altering characteristics; and
  using the correlated results from the uncertainty analysis to select the brine composition with the at least one reducing agent to inject into the formation to enhance recovery of the hydrocarbons from the formation.

2. The method of claim 1, wherein the uncertainty analysis comprises sessile drop tests, contact angle tests, spreading coefficient tests, zeta potential tests, soaking at least some of the plurality of the substrates in some of the plurality of the brine compositions for predetermined periods of times before adding any of the plurality of the reducing agents to these brine compositions, adding a droplet of oil to at least one soaked substrate, adding a predetermined amount of a particular reducing agent to a particular brine composition and analyzing changes in wettability of a particular substrate, or any combination thereof.

3. The method of claim 1, wherein the uncertainty analysis comprises Design of Experiments, Karhunen-Loeve transform, Principal Component Analysis (PCA), sensitivity analysis, or any combination thereof.

4. The method of claim 1, wherein the at least one reducing agent is selected from a salt of carbonate, nitrate, bisulfite, meta bisulfite, dithionite, sulfate, metaborate, or any combination thereof.

5. The method of claim 1, wherein the oxyanions are selected from carbonate ($CO_3^{2-}$), nitrate ($NO_3^-$), meta-bisulfite ($[S_2O_5]^{2-}$), bisulfite ($HSO_3^-$), dithionite ($[S_2O_4]^{2-}$), sulfate ($SO_4^{2-}$), metaborate ($BO_2^-$), or any combination thereof.

6. The method of claim 5, further comprising injecting the selected brine composition with the at least one reducing agent into the formation to alter wettability at the surface of the formation to enhance recovery of the hydrocarbons from the formation.

7. The method of claim 6, wherein the at least one reducing agent is present in the selected brine composition in an amount of less than 5,000 ppm.

8. The method of claim 6, wherein the at least one reducing agent is present in the selected brine composition in an amount ranging from 50 ppm to 3,500 ppm.

9. The method of claim 6, further comprising de-aerating and de-oxygenating the selected brine composition prior to the addition of the at least one reducing agent.

10. The method of claim 6, wherein the formation is a carbonate formation, a siliceous formation, or any combination thereof.

11. The method of claim 6, further comprising providing a surfactant to the selected brine composition with the at least one reducing agent.

12. The method of claim 6, further comprising providing a mobility control agent to the selected brine composition with the at least one reducing agent.

13. The method of claim 12, wherein the mobility control agent comprises a foam.

14. The method of claim 12, wherein the mobility control agent comprises a polymer.

15. The method of claim 12, further comprising providing a surfactant to the selected brine composition with the at least one reducing agent.

* * * * *